United States Patent [19]

Kudzma et al.

[11] Patent Number: 4,921,864
[45] Date of Patent: May 1, 1990

[54] 4-PHENYL-4-(N-(PHENYL)AMIDO) PIPERIDINE DERIVATIVES AND PHARMACEUTICAL COMPOSITIONS AND METHOD EMPLOYING SUCH COMPOUNDS

[75] Inventors: Linas V. Kudzma, North Bergen; H. Kenneth Spencer, Chatham; Sherry A. Severnak, Plainfield, all of N.J.

[73] Assignee: BOC, Inc., New Providence, N.J.

[21] Appl. No.: 255,180

[22] Filed: Oct. 7, 1988

Related U.S. Application Data

[62] Division of Ser. No. 115,284, Nov. 2, 1987, U.S. Pat. No. 4,791,121.

[51] Int. Cl.⁵ .................. C07D 409/12; A61K 31/445
[52] U.S. Cl. ...................................... 514/326; 546/213
[58] Field of Search .......................... 546/213; 514/326

[56] References Cited

U.S. PATENT DOCUMENTS

| | | | |
|---|---|---|---|
| 3,161,637 | 12/1964 | Janssen et al. | 546/213 |
| 3,164,600 | 1/1965 | Janssen | 546/213 |
| 3,998,834 | 12/1976 | Janssen | 546/213 |
| 4,196,210 | 4/1980 | Sanczuk et al. | 546/213 |
| 4,584,303 | 4/1986 | Huang et al. | 546/210 |

*Primary Examiner*—Mary C. Lee
*Assistant Examiner*—Zinna Northington Davis
*Attorney, Agent, or Firm*—R. Hain Swope; Larry R. Cassett

[57] ABSTRACT

Compounds are disclosed of the formula

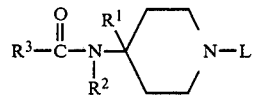

where $R^2$ is unsubstituted or substituted phenyl, $R^3$ is lower alkyl, lower cycloalkyl or lower alkoxy lower alkyl, and L is selected from a wide variety of groups. This new class of compounds exhibit improved analgesic and anesthetic properties.

8 Claims, No Drawings

4-PHENYL-4-(N-(PHENYL)AMIDO) PIPERIDINE DERIVATIVES AND PHARMACEUTICAL COMPOSITIONS AND METHOD EMPLOYING SUCH COMPOUNDS

This is a division of Application Ser. No. 07/115,284 filed on Nov. 2, 1987, now U.S. Pat. No. 4,791,121.

BACKGROUND OF THE INVENTION

The present invention relates to 4-phenyl-4-[N-(phenyl)amido] piperidine and derivatives and methods and compositions employing such compounds. In particular, this new class of compounds has been found to possess desirable analgesic and anesthetic properties.

A number of patents disclose certain N-phenyl-N-(4-piperidinyl)amides having analgesic activity. For example, some such compounds are disclosed in U.S. Pat. Nos. 3,164,600 and 3,998,834. P. Janssen in U.S. Pat. No. 3,164,600 discloses such compounds in which the 4 position of the piperidine ring is substituted by a lower alkyl. The latter patent does not disclose compounds where the 4-piperidine position is occupied by an aryl or phenyl ring system.

According to the report of S. McElvain et al., JACS, Vol. 80 (Aug. 5, 1958) a change in the 4-position of certain substituted piperidines generally leads to less or no analgesic activity. For example, McElvain et al. teaches that in going from methyl to butyl there is no apparent effect on the degree of analgesia, and the 4-phenyl substituent fails to produce any marked effect.

SUMMARY OF THE INVENTION

Compounds of the present invention possess potent analgesic and anesthetic properties. Preferred compounds of the present invention when administered to mammals allow rapid recovery including early regain of muscle coordination.

Respiratory depression during use is relatively low or absent compared to commonly known intravenous anesthetics such as fentanyl. Heart rate decrease and arterial pressure decrease are also less. The present compounds are therefore safer, particularly when a patient may have a coronary deficiency.

It has now been found that very desirable narcotic agonist properties are provided by compounds of the formula:

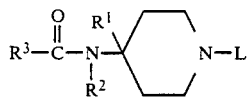 (I)

optically active isomeric forms thereof, and/or pharmaceutically acceptable acid addition salts thereof. In the Formula (I) above, $R^1$ is phenyl; $R^2$ is phenyl, unsubstituted or substituted by one or more halogen groups; $R^3$ is a lower alkyl, or lower cycloalkyl or a lower alkoxy lower alkyl; and L is one of a variety of groups including thienyl lower alkyl, thiazolyl lower alkyl which can be substituted in the 4-position with a lower alkyl, (4,5-di-hydro-5-oxo-1H-tetrazol-1-yl) lower alkyl which can be substituted in the 4-position with a lower alkyl, 1H-pyrazolyl lower alkyl, 2-(1,2-dihydro-2-oxo-3H-benzoxazolyl, pyridyl lower alkyl, 5-nitro-1H-imidazol-1-yl lower alkyl substitued in the 2 position by a lower alkyl, 1H-pyrazolyl lower alkyl substituted in the 4 position by a halogen, lower alkenyl, lower alkyl cycloalkyl and phenyl lower alkyl.

A preferred class of compounds within the scope of the present invention are of the formula

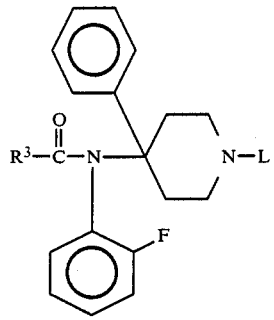

optically active isomeric forms thereof, and/or pharmaceutically acceptable acid addition salts thereof, in which formula: $R^3$ is lower alkyl, lower cycloalkyl or lower alkoxy lower alkyl both of 2–6 carbon atoms; and L is phenyl lower alkyl, thiazolyl lower alkyl substituted in the 4-position with a methyl group, 4,5-di-hydro-5-oxo-1H-tetrazol-1-yl, the latter substituted in the 4-position with an ethyl group, or thienyl lower alkyl.

DETAILED DESCRIPTION OF THE INVENTION

As noted above, the compounds of the invention have the formula

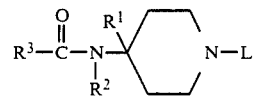

wherein $R^1$ is phenyl and $R^2$ is phenyl, either unsubstituted or substituted by one or more halogens; $R^3$ is a lower alkyl, lower cycloalkyl, or a lower alkoxy lower alkyl group; and L is one of a variety of groups including thienyl lower alkyl, thiazolyl lower alkyl which can be substituted in the 4-position with a lower alkyl group, (4,5-di-hydro-5-oxo-1H-tetrazol-1-yl) lower alkyl which can be substituted in the 4-position with a lower alkyl, 1H-pyrazolyl lower alkyl, 2-(1,2-dihydro-2-oxo-3H-benzoxazolyl, pyridyl lower alkyl, 5-nitro-1H-imidazol-1-yl lower alkyl substitued in the 2 position by a lower alkyl, 1H-pyrazolyl lower alkyl substituted in the 4 position by a halogen, lower alkenyl, lower alkyl lower cycloalkyl and phenyl lower alkyl. The compounds can be in the form of pharmaceutically acceptable acid addition salts, optically active isomers, and/or cis/trans isomers thereof.

The preferred $R^2$ groups is 2-fluorophenyl.

The group $R^3$ in Formula I above is a lower alkyl or a lower alkoxy lower alkyl. Examples of suitable $R^3$ groups include methoxymethyl, ethoxymethyl, 1-propoxymethyl, 2-propoxymethyl, 1-butoxymethyl, 1-pentoxymethyl, 1-hexoxy-methyl, 1-heptoxymethyl, 1-methoxyethyl, 1-ethoxy-1-ethyl, 1-butoxy-1-ethyl, methyl, ethyl, propyl, butyl, pentyl, or hexyl. A preferred $R_1$ group is methyl, ethyl, methoxy or ethoxy.

In Formula I above, suitable L groups include 3-propene, cyclopropyl methyl, 2-phenylethyl, 1-phenyl-2- propyl, and 2-phenyl-1-propyl, 2-(4,5-di-hydro-5-oxo-1H-tetrazol-1-yl) ethyl substituted in the 4-position with ethyl, and thiazolyl lower alkyl substituted in the 4-position with methyl, 2-(2-thienyl)ethyl, 2-(3-thienyl)ethyl, 2-(1H-pyrazol-1-yl)ethyl, 2-(1,2-dihydro-2-oxo-3H-benzoxazol-3-yl)ethyl, 2-(4-methyl-thiazol-5-yl)ethyl, 2-(2-pyridyl) ethyl, 2-(2-methyl-5-nitro-1H-imidazol-1-yl)ethyl and 2-(4-iodo-1H-pyrazol-1-yl)ethyl.

By lower alkyl or lower alkoxy groups or lower alkyl cycloalkyl, we mean branched, unbranched or aliphatic cyclic containing groups, containing from 1 to 7 carbon atoms and preferably 1 to 4 carbon atoms. By lower alkenyl is meant branched, or unbranched unsaturated groups containing 1 to 7 carbon atoms and preferably 1 to 4 carbon atoms.

The compounds of the invention can exist in the form of the free base or the therapeutically or pharmaceutically acceptable acid addition salts by treatment with an appropriate acid, such as an inorganic acid, e.g., hydrochloric, hydrobromic, sulfuric, nitric, phosphoric acids and the like; or an organic acid such as acetic, trifluoroacetic, propionic, hydroxyacetic, methoxyacetic, benzoic, citric, oxalic, methanesulfonic, ethanesulfonic, benzenesulfonic, toluenesulfonic, succinic, tartaric, and the like acids. Preferred acid addition salts are the chloride and oxalate or citrate. These acid addition salts can be prepared by conventional methods, e.g., by treatment with the appropriate acid.

Compounds of the invention having at least one asymmetric carbon atom can exist in optionally active isomeric forms. For example, in compounds in which L is a 1-phenyl-2-propyl group, the carbon adjacent to the piperidinyl nitrogen is an asymmetric carbon and such compounds can therefore exist in optical active isomeric (enantiomeric) forms. Such isomeric forms can be isolated from the racemic mixtures by techniques known to those skilled in the art.

The compounds of the invention, prepared as the free base, can be combined with a pharmaceutically acceptable carrier to provide a pharmaceutical composition. Suitable carriers for the free bases include propylene glycol-alcohol-water, isotonic water, sterile water for injection, USP, emulphor TM-alcohol-water, cremophor-EL TM or other carriers known to those skilled in the art.

The compounds of the invention prepared as the pharmaceutically acceptable acid addition salts can also be combined with a pharmaceutically acceptable carrier to provide a pharmaceutical composition. Suitable carriers for the acid addition salts may include an isotonic aqueous solution, or sterile water for injection, USP, alone or in combination with other solubilizing agents such as ethanol, propylene glycol, or other conventional solubilizing agents known to those skilled in the art. Of course, the carrier will vary depending upon the mode of administration desired for the pharmaceutical composition as is conventional in the art. A preferred carrier is an isotonic aqueous solution containing from 0.0001 mg/ml to 0.5 mg/ml of at least one of the compounds of this invention depending upon the pharmacology of the individual compounds being employed in the formulation.

The compounds of the invention can be administered to mammals, e.g., animals or humans, in amounts effective to provide the desired therapeutic effect. The compounds can be administered intravenously, intramuscularly or subcutaneously in the previously described carriers. These compounds may also be administered orally, sublingually, rectally, or transcutaneously with a suitable pharmaceutically acceptable carrier for that mode of administration as is conventional in the art.

As noted above, an effective amount of the compounds of the present invention is employed to obtain the desired therapeutic effect. Since the activity of the compounds and the depth of the desired therapeutic effect vary, the dosage level employed of the compound also varies. The actual dosage administered will be determined by such generally recognized factors as the body weight of the patient or the idiosyncrasies of the particular patient. Thus, the unit dosage for a particular patient (man) can be as low as (0.00005 mg/Kg,) which the pracitioner may titrate to the desired effect.

The compounds of the present invention can be prepared beginning with known piperidones as shown below:

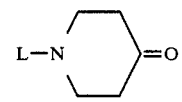

For example, the compound 4-(2-phenylethyl)-piperidone can be prepared according to the procedure published by A. H. Becket, A. F. Casey and G. Kirk, *J. Med Pharm. Chem.*, Vol. 1, 37 (1959). The compound 4-benzyl-1-piperidone can be prepared in an analogous manner by the procedures described by C. R. Ganellin and R. G. Spickch, *J. Med. Chem.*, Vol. 8, 619 (1965) or P. M. Carabateas and L. Grumbach, *J. Med. Pharm. Chem.*, Vol. 5, 913 (1962). Compounds with other L groups can be prepared as disclosed in U.S. Pat. No. 4,584,303 herein incorporated by reference.

In one example of a process of the invention, L-piperidone may be reacted with phenyl amine and the resulting Schiff base may be further reacted with, for example, phenyl lithium to give 4-phenyl-amino-piperidine or the corresponding substituted phenyl if the substituted substituted phenyl amine is used. The following reaction scheme illustrates such a method:

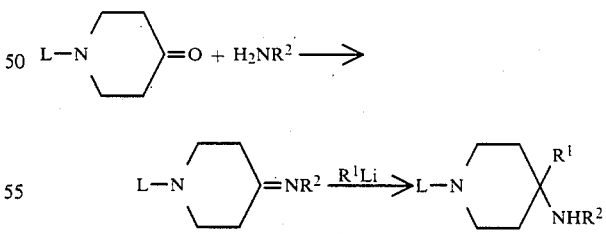

The latter compound can be reacted with the appropriate acid halide, e.g. $R^3(COCl)$ or anhydride $(R^3CO)_2O$ to introduce the appropriate $R^3$—CO— group onto the amino nitrogen as follows.

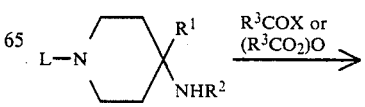

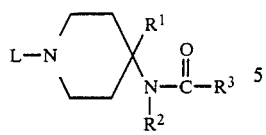 5

L may originally be phenylmethyl and when L is not phenylmethyl in the final product, one procedure for preparing compounds of the present invention is to subsequently split off the benzyl group and replace it with the desired L group. For example, the compounds of the invention may be prepared when starting with 1-(2-phenylmethyl)-4-piperidone by the following reaction scheme:

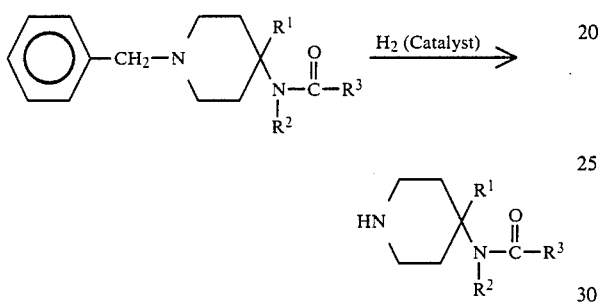

An alternative method of replacing the L group involves employing alpha-chloro-ethylchloroformate to accomplish debenzylation followed by methanolysis.

The appropriate L group can then be introduced by reacting the latter compound with an appropriately reactive molecule LX wherein X is, for example, halogen such as chlorine, bromine or iodine, e.g., as illustrated below

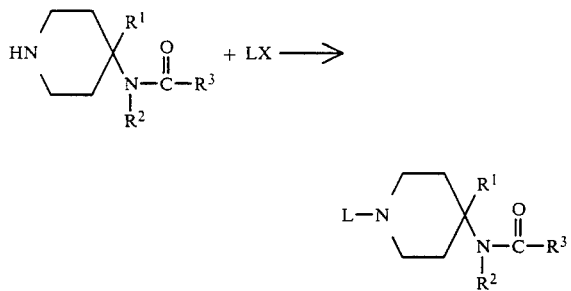

The reaction of LX can be conducted in an inert organic solvent such as, for example, N,N-dimethylformamide (DMF) or acetonitrile in the presence of an appropriate base such as alkali metal carbonate.

Compounds of the invention may also be prepared via a nitrile intermediate by the following reaction scheme:

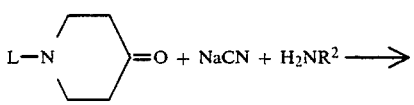

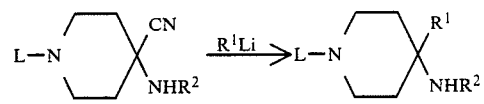

The remaining steps may proceed as shown above.

The following examples are presented for the purposes of demonstrating, but not limiting the compounds or compositions of this invention.

EXAMPLE 1

1-Benzyl-4-piperidone (61.50 gms, 325 mmol, Aldrich 99%+) and 2-fluoroaniline (37.80 gms, 340 mmol, Aldrich 99%) were combined in 300 mls of toluene and p-toluenesulfonic acid monohydrate (1 gm, Aldrich 99%) was added. The reaction was refluxed overnight under argon separating water in a Dean-Stark trap. After 18 hrs. of reflux the theoretical amount of water (5.8 ml) was collected and drained from trap. Approximately 150 mls. of toluene were distilled from the reaction mixture and the reaction was cooled to RT under argon. The resulting viscous dark-orange solution of the following crude schiff base was obtained.

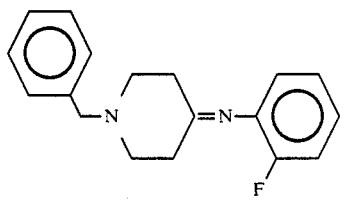

EXAMPLE 2

The crude schiff base/toluene solution from Example 1 (325 mmol) was added as a slow stream via large bore cannula to a cold (0° C.) solution of 2.0M phenyllithium in cyclohexane/ethyl ether 7:3 (325 ml, 650 mmol, Aldrich) under argon. Addition was complete after 20 min. and the reaction mixture was stirred at 0° C. for an additional 0.5 hrs. The reaction was quenched by slow dropwise addition of 300 mls of water (exothermic) with stirring and cooling. The bilayer solution was then stirred for 0.5 hrs. to dissolve solids and the organic layer was separated. The aqueous layer was extracted twoce with 125 ml portions of toluene. The 3 organic layers were combined, dried (Na$_2$SO$_4$) and concentrated to give the desired diamine (Rf 0.6 EtOAc/Hex) as a dark brown oil. The oil was applied to a 4″ diameter column packed with 900 gms of Silica 60 (230-400 mesh) and the column was eluted with 1:10 EtOAc/Hex to give the following diamine as a yellow oil which solidified upon standing several days (60.33 gms, 51.5%).

1-benzyl-4-phenyl-4-[N-(2-fluorophenyl)]piperidine.
mp: 101°-102° C.
%CHN
Calc.: %C(79.74), %H(7.25), %N(7.75).
Found: %C(79.75), %H(6.98), %N(7.82).
NMR: 7.80-5.90 (complex, 14H), 4.50(br s, 1H), 3.50(s, 2H), 3.00-1.90 (complex, 8H).

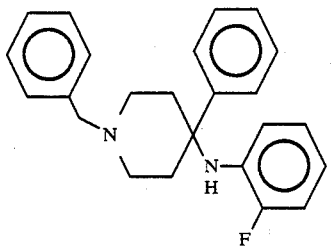

The diamine can be crystallized as follows. The solid diamine (219.37 gms) was suspended in 600 mls of stirring hexane and the hexane was heated to boil. The clear pale yellow solution was cooled slowly to RT overnight to give clusters of long needles along with large solid crystals at the bottom of the flask. The crystalline solids were filtered, washed with cold hexane and dried in vacuum overn (1 hr, 50° C.) to give pale yellow crystals of pure diamine. Recovery was 147.87 gms (67.4%).

EXAMPLE 3

40.95 gms (113.6 mmol) of the diamine of Example 2 was dissolved in 500 ml of chloroform. This solution was stirred at RT and 100 ml (1.15 mol) of propionyl chloride was added rapidly dropwise. Approximately 3 minutes following the addition of the acid chloride, the reaction mixture turned cloudy and gradually turned to a thick white paste. Stirring was maintained and the reaction mixture was heated to a gentle reflux. After overnight reflux, the reaction mixture was less viscous and stirred more easily. Reflux was continued for two weeks, removing small aliquots every few days to monitor by TLC the disappearance of starting diamine. After 15 days at reflux the reaction mixture turned clear and the now golden yellow solution was refluxed one more day to reveal virtually no remaining starting diamine. The reaction mixture was cooled to RT and added slowly dropwise (exothermic) to a cold stirring solution of 10% NaOH (total of 2.5 mol NaOH). The bilayer solution was vigorously stirred for several hours followed by separation of the organic layer which was dried over $Na_2SO_4$, filtered and concentrated to give the following amide as an amber glas (50.58 gms, contains trapped solvent, yield >95%).

1-benzyl-4-phenyl-4-[N-(2-fluorophenyl)propionamido] piperidine.

NMR: 7.90-7.00 (m, 14H), 3.30(s, 2H), 3.25-1.50-(complex, 10H), 0.80(t, 3H).

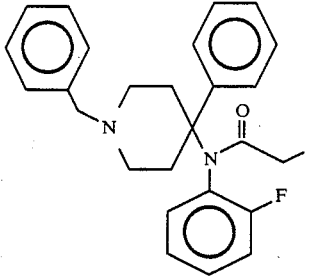

EXAMPLE 4

The amide of Example 3 (29.7 gms, 71.3 mmol) was dissolved in 400 ml 1,2-dichloroethane and cooled in ice bath under argon. 1-Chloroethyl chloroformate (12 gms, 83.9 mmol) was added dropwise to the cold solution and the reaction mixture was stirred at 0° C. for 15 min. followed by warming to RT. The reaction was then heated to reflux, After 2 hrs. at reflux, the reflux condenser was changed for a still head and approximately ¾ of the solvent was distilled off. The remaining reaction mixture was diluted with 200 mls of methanol and heated to reflux for 5 hrs. followed by cooling and stirring overnight at RT. The reaction was then concentrated in vacuo and residue was taken up in 0.5N HCl (1000 ml). The aqueous solution was washed twice with 300 ml portions of ethyl ether. The aqueous layer was basified with 25% NaOH and extracted with chloroform. The chloroform layer was separated and concentrated to give the following nor-compound (18.62 gms, 80%).

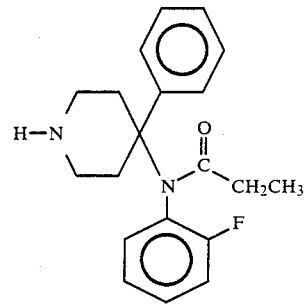

EXAMPLE 5

The nor-compound obtained in Example 4 (24.5 gms, 75.41 mmol) was dissolved in 250 ml of acetonitrile. To this solution was added $K_2CO_3$ (24 gms) followed by a bromoethyltetrazoleinone, specifically 1-(2-Bromoethyl)-4-ethyl-1,4 dihydro-5H-tetrazol-5-one (17.77 gms, 80.38 mmol). The reaction mixture was then heated to reflux. After 2 days at reflux the reaction was cooled and filtered. The filtrate was concentrated in vacuo and the residue was chromatographed on a column of 350 gms. of silica 60 (230-400 mesh) eluting with 2:1 EtOAc/Hex. Fractions were monitored by TLC. Fractions containing desired compound (Rf 0.2 2:1 EtOAc/Hex) were combined and concentrated to give 25.8 gms of the following compound (73.6%) as a light brown oil. This oil can be crystallized from hot t-butyl methyl ether, if so desired, as follows.

The compound (53.04 gms, 113.68 mmol) was dissolved in 1500 ml of ethyl ether with 300 ml THF added to enhance solubility. This solution was stirred under argon and freshly prepared HCl etherate (1 gm HCl/50 ml) was added dropwise very slowly to avoid any local excess of HCl in the solution. The pH of the solution was monitored with pH paper and the addition of HCl etherate was stopped when the solution was just acid. The white solid was filtered, washed with ether and dried under vacuum at RT overnight. The fluffy white power was then suspended in 450 ml t-butyl methyl ether and heated to boil. Methanol (50 ml) was added to the hot solution to dissolve the solids. The now clear solution was then cooled to RT followed by refrigeration for 3 days. The resultant crystalline solid was collected, washed with ethyl ether and dried in vacuum oven (overnight at 80° C.) to give 49.76 gms. of white solid, m.p. 199°–201° C.

1-[2-(4-ethyl-4,5-dihydro-5-oxo-1H-tetrazol-1-yl)ethyl]-4-phenyl-4-[N-(2-fluorophenyl)propionamido]-piperidine.

%CHN analysis of oxalate salt mp=200° C. Calc.: %C(58.26), %H(5.97), %N(15.10). Found: %C(58.24), %H(5.91), %N(15.03).

NMR: 7.90–7.00(m, 9H), 4.30–3.80(m, 4H), 3.50–1.70 (complex, 12H), 1.35(t, 3H), 1.85(t, 3H).

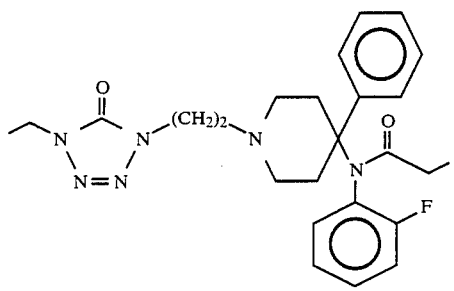

EXAMPLES 6–12

Further examples of compounds within the scope of the present invention which were prepared by procedures analogous to those described included the following:

| COMPOUND | M.P. |
|---|---|
| 6. 1-(2-phenylethyl)-4-phenyl-4-[N-(2-fluorophenyl) cyclopropylcarboxamido]piperidinium oxalate; | 209–210° C. |
| 7. 1-[2-(4-ethyl-4,5-dihydro-5-oxo-1H-tetrazol-1-yl)ethyl]-4-phenyl-4-[N-(2-fluorophenyl)cyclopropylcarboxamido]piperidinium oxalate; | 190–191° C. |
| 8. 1-[2-(1H-pyrazol-1-yl)ethyl]-4-phenyl-4-[N-(2-fluorophenyl)cyclopropylcarboxamido]piperidinium oxalate; | 214–215° C. |
| 9. 1-[2-(4-ethyl-4,5-dihydro-5-oxo-1H-tetrazo-1-yl)ethyl]-4-phenyl-4-[N-(2-chlorophenyl)propionamido]piperidinium oxalate; | 186–187° C. |
| 10. 1-allyl-4-phenyl-4-(N-phenylmethoxyacetamido) piperidinium oxalate; | 191° C. |
| 11. 1-(cyclopropyl)methyl-4-phenyl-4-(N-phenylmethoxyacetamido) piperidinium oxalate; | 201–202° C. |
| 12. 1-[2-(4-ethyl-4,5-dihydro-5-oxo-1H-tetrazol-1-yl)ethyl]-4- phenyl-4-(N-phenylmethoxyacetamido) piperidinium oxalate; | 185–187° C. |

EXAMPLES 13–26

A number of compounds in accordance with the present invention were tested for their analgesic and reversal properties. Specifically, the acid addition oxalate salts of the compounds tested in accordance with the invention were dissolved in sterile water for injection, USP, to form a solution whose concentration varied from 0.00001 mg/ml to 5 mg/ml. The solution was administered intravenously in a mouse tail vain.

The $ED_{50}$ values were obtained from the mouse hot plate analgesia test (58° C.) described in Domer, Floyd R., *Animal Experiments in Pharmacological Analysis*, Charles C. Thomas, Springfield, 1971, p. 283 ff. The compounds listed in Table 1 below were tested by this procedure and found to have the analgesic activities listed in Table 1.

TABLE

| Compound | M.P. °C. | Analgesic Activity $(ED_{50})$mg/Kg Mice |
|---|---|---|
| 13. 1-(2-phenylethyl)-4-phenyl-4-[N-(2-fluorophenyl)propionamido] piperidinium oxalate | 207–8° C. | 0.0145 |
| 14. 1-[2-(2-thienyl)ethyl]-4-phenyl-4-[N-(2-fluorophenyl)propionamido] piperidinium oxalate | 199–201 | 0.0066 |
| 15. 1-[2-(4-ethyl-4,5-dihydro-5-oxo-1H-tetrazol-1-yl)ethyl]-4-phenyl-4-(N-(2-fluorophenyl)propionamide] piperidinium chloride | 197–197.5 | 0.082 |
| 16. 1-[2-(1H-pyrazol-1-yl)ethyl]-4-phenyl-4-[N-(2-fluorophenyl)propionamide] piperidinium oxalate | 200–201 | 0.026 |
| 17. 1-[2-(1,2-dihydro-2-oxo-3H-benzoxazol-3-yl)ethyl]-4-phenyl-4-[N-(2-fluorophenyl) propionamide] piperidinium oxalate | 216–218 | 0.435 |
| 18. 1-[2-(4-methyl-thiazol-5-yl)ethyl]-4-phenyl-4-[N-(2-fluorophenyl)propionamide] piperidinium oxalate | 227–228 | 0.0074 |
| 19. 1-(2-phenylethyl)-4-phenyl-4-[N-(phenyl) propionamide] piperidinium oxalate | 223–224 | 0.011 |
| 20. 1-[2-(2-thienyl)ethyl)-4-phenyl-4-[N-(phenyl)propionamide] piperidinium oxalate | 204.5–206 | 0.014 |
| 21. 1-[2-(3-thienyl)ethyl]-4-phenyl-4-[N-(phenyl)propionamide] piperidinium oxalate | 224–224 | 0.0014 |
| 22. 1-[2-(1H-pyrazol-1-yl)ethyl]-4-phenyl-4-[N-(phenyl)propionamide] piperidinium oxalate | 193–195 | 0.043 |
| 23. 1-[2-(4-ethyl-4,5-dihydro-5-oxo-1H-tetrazol-1-yl)ethyl]-4-phenyl-4-[N-(phenyl)propionamide] piperidinium oxalate | 183–185 | 0.275 |
| 24. 1-[2-(2-pyridyl)ethyl]-4-phenyl-4-[N-(phenyl)propionamide]piperidinium oxalate | 174–175 | 0.026 |
| 25. 1-[2-(2-methyl-5-nitro-1H-imidazol-1-yl)ethyl]-4-phenyl-4-[N-(2-fluorophenyl)pro- | 225° C. | 0.175 |

TABLE-continued

| Compound | M.P. °C. | Analgesic Activity (ED$_{50}$)mg/Kg Mice |
|---|---|---|
| pionamido]piperidinium oxalate | | |
| 26. 1-[2-(4-iodo-1H-pyrazol-1-yl)ethyl]-4-phenyl-4-[N-(2-fluorophenyl)propionamido]-piperidinium oxalate | 219–220 | 0.023 |

It will be understood that the embodiments described herein are merely exemplary and that a person skilled in the art may make many variations and modifications without departing from the spirit and scope of the invention. All such modifications and variations are intended to be included within the scope of the invention as defined in the appended claims.

We claim:

1. A compound of the formula

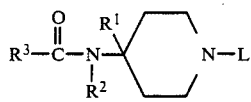

optically active isomeric forms thereof, or pharmaceutically acceptable acid addition salts thereof, in which formula: $R^1$ is phenyl; $R^2$ is phenyl unsubstituted or substituted with one or more halogens; $R^3$ is a lower alkyl, lower cycloalkyl or a lower alkoxy lower alkyl; and L is thienyl lower alkyl which can be substituted in the 4-position with a lower alkyl group.

2. A compound according to claim 1, which comprises 1-[2-(2-thienyl)ethyl]-4-phenyl-4-[N-(2-fluorophenyl)propionamido]piperidine or a pharmaceutically acceptable addition salt thereof.

3. A compound according to claim 1, which comprises 1-[2-(2-thienyl)ethyl]-4-phenyl-4-[N-(phenyl)propionamido]piperidine or a pharmaceutically acceptable addition salt thereof.

4. A compound according to claim 1, which comprises 1-[2-(3-thienyl)ethyl]-4-phenyl-4-[N-(phenyl)propionamide]piperidine or a pharmaceutically acceptable addition salt thereof.

5. A narcotic antagonistic or analgesic composition comprising a non-toxic pharmaceutically acceptable carrier and therapeutically effective amount of a compound of the formula

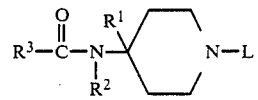

optically active isomeric forms thereof, or pharmaceutically acceptable acid addition salts thereof, in which formula: $R^1$ is phenyl; $R^2$ is phenyl unsubstituted or substituted by one or more halogens; $R^3$ is a lower alkyl, lower cycloalkyl or a lower alkyl; and L is a thienyl lower alkyl group which can be substituted in the 4-position with a lower alkyl group.

6. A composition according to claim 5, which comprises 1-[2-(2-thienyl)ethyl]-4-phenyl-4-[N-(2-fluorophenyl)propionamido]piperidine or a pharmaceutically acceptable addition salt thereof.

7. A composition according to claim 5, which comprises 1-[2-(2-thienyl)ethyl]-4-phenyl-4-[N-(phenyl)propionamide]piperidine or a pharmaceutically acceptable addition salt thereof.

8. A composition according to claim 5, which comprises 1-[2-(3-thienyl)ethyl]-4-phenyl-4-[N-(phenyl)propionamide]piperidine or a pharmaceutically acceptable addition salt thereof.

* * * * *

UNITED STATES PATENT AND TRADEMARK OFFICE
CERTIFICATE OF CORRECTION

PATENT NO. : 4,921,864
DATED : May 1, 1990
INVENTOR(S) : Linas V. Kudzma et al.

It is certified that error appears in the above-identified patent and that said Letters Patent is hereby corrected as shown below:

Column 11, lines 30-31, delete "which can be substituted in the 4-position with a lower alkyl group".

Column 12, lines 27-28, delete "which can be substituted in the 4-position with a lower alkyl group".

Signed and Sealed this

First Day of October, 1991

Attest:

HARRY F. MANBECK, JR.

Attesting Officer

Commissioner of Patents and Trademarks